United States Patent [19]

Kochi

[11] Patent Number: 5,036,103

[45] Date of Patent: Jul. 30, 1991

[54] METHOD OF TREATING CANCER CELLS IN HUMANS

[76] Inventor: Matsuyuki Kochi, 19, Matsudo Shinden, Matsudo-shi, Chiba-ken, Japan

[21] Appl. No.: 560,221

[22] Filed: Jul. 25, 1990

Related U.S. Application Data

[63] Continuation of Ser. No. 351,284, May 8, 1989, abandoned, which is a continuation of Ser. No. 214,811, Jul. 5, 1988, abandoned, which is a continuation of Ser. No. 883,666, Jul. 9, 1986, abandoned, which is a continuation-in-part of Ser. No. 683,477, Dec. 19, 1984, abandoned.

[30] Foreign Application Priority Data

Dec. 27, 1983 [JP] Japan .................................. 58-244787

[51] Int. Cl.$^5$ ............................................ A61K 31/375
[52] U.S. Cl. ................................................... 514/467
[58] Field of Search ........................ 514/467; 549/315

[56] References Cited

U.S. PATENT DOCUMENTS 4,552,888 11/1985 Koppel et al. ...................... 514/467

OTHER PUBLICATIONS

The Merck Index, 10th edition, Rahway, N.J., 8411 (1983).

Primary Examiner—Nicky Chan
Attorney, Agent, or Firm—Larson and Taylor

[57] ABSTRACT

A method of treating or inhibiting cancer cells grown in the pancreas, liver, kiidney, lymph glands, salivery glands, breast, lung and stomach of humans, which comprises administering an effective amount of a sodium salt, potassium salt or calcium salt of 5,6-O-benzylidene-L-ascorbic acid to a human who is suffering from the growth of cancer cells in the body of the patient.

8 Claims, No Drawings

METHOD OF TREATING CANCER CELLS IN HUMANS

CROSS-FEFERENCE TO RELATED APPLICATIONS

This application is a continuation of application Ser. No. 07/351,284 filed 05/08/89, abandoned, which is a continuation of Ser. No. 214,811, filed July 5, 1988, abandoned, which is a continuation of application Ser. No. 06/883,666 filed 07/09/86, abandoned, which is a CIP of Ser. No. 06/683,477 filed 12/19/84, abandoned.

SUMMARY OF THE INVENTION

This invention relates to a method of treating or inhibiting cancer cells in the pancreas, liver, kidney, lymph glands, salivary glands, breast, lung and stomach of humans, by administration of an alkali metal or alkaline earth metal salt of 5,6-O-benzylidene-L-ascorbic acid.

BACKGROUND OF THE INVENTION

That a known compound, 5,6-O-benzylidene-L-ascorbic acid of the formula

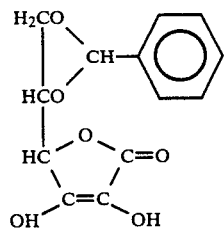

as described in the "Steroids" 12, 309 (1968) is active as an anti-tumor agent and that the new sodium salt, new potassium salt and new calcium salt of the 5,6-O-benzylidene-L-ascorbic acid are also active as an anti-tumor agent are described in the specification of U.S. patent application Ser. No. 683,477 of which the joint-inventors include me. The specification of this pending U.S. patent application also describes that the alkali metal salts and the alkaline earth metal salt of 5,6-O-benzylidene-L-ascorbic acid are readily soluble in water and their aqueous solutions show a pH value of nearly 7.0 and may be administered as injectable aqueous solutions; and further that the anti-tumor activity of the sodium salt of 5,6-O-benzylidene-L-ascorbic acid was tested against fibro-sarcoma Meth-A cells (mouse solid tumor) as implanted in mice. There is also described a particular process of producing 5,6-O-benzylidene-L-ascorbic acid and a metal salt thereof, which process comprises reacting L-ascorbic acid with α,α-dimethoxytoluene to produce 5,6-O-benzylidene-L-ascorbic acid, in the presence of an acid catalyst such as p-toluenesulfonic acid under heating and in an inert organic solvent such as dimethylformamide, dimethylsulfoxide and the like.

The preparation of the metal salts of 5,6-O-benzylidene-L-ascorbic acid may conveniently be performed by suspending crystals of 5,6-O-benzylidene-L-ascorbic acid in water, and adding to the resultant aqueous suspension an equi-molar proportion of an alkaline metal compound such as sodium compound, for example, sodium hydrogen carbonate, followed by stirring the mixture, so that the crystals may dissolve in water and undergoes the salt-forming reaction. The resulting reaction solution may then be either lyophilized or added with an organic solvent such as isopropanol in which the sodium salt of 5,6-O-benzylidene-L-ascorbic acid is sparingly soluble, to deposit sodium salt of 5,6-O-benzylidene-L-ascorbic acid as white to pale pink colored crystals. Similarly, the potassium salt of 5,6-O-benzylidene-L-ascorbic acid may be obtained by reaction of 5,6-O-benzylidene-L-ascorbic acid with potassium hydrogen carbonate, and the calcium salt of 5,6-O-benzylidene-L-ascorbic acid by reaction of 5,6-O-benzylidene-L-ascorbic acid with ½ molar proportion of calcium carbonate.

The production of 5,6-O-benzylidene-L-ascorbic acid and the alkali metal and alkaline earth metal salts thereof is illustrated in the pending U.S. patent application Ser. No. 683,477 with reference to the following Examples 1 to 4.

EXAMPLE 1

Production of 5,6-O-benzylidene-L-ascorbic acid;

L-Ascorbic acid (20 g), α,α-dimethoxytoluene (20 g) and a catalytic quantity (160 mg) of p-toluenesulfonic acid were dissolved in 60 ml of dimethylformamide. The solution was heated at 55°-60° C. for 4 hours. The reactor used for carrying out the reaction was equipped with a reflux-condenser connected to an aspirator, and the methanol formed during the reaction process produces was evaporated out of the reaction mixture. When the reaction was completed, the reaction solution was distilled under reduced pressure to remove the solvent. The resulting syrupy residue was washed with petroleum ether and water, each three times. Then, water and hexane were added to the washed syrup and the mixture was stirred to obtain a crystalline product of 5,6-O-benzylidene-L-ascorbic acid which was then filtrated off and dried to give 21.5 g of white colored crystals of 5,6-O-benzylidene-L-ascorbic acid (72% yield). The product thus obtained was nearly pure substance but was further purified by recrystallization from methanol or benzene. The final pure crystal showed mp. of 166°-168° C.

EXAMPLE 2

5,6-O-Benzylidene-L-ascorbic acid (20 g) was suspended in 320 ml of water, to which was then added a powder of sodium hydrogen carbonate (6.4 g), so that the whole mixture became a clear solution after bubbling. The solution obtained was lyophilized to afford a sodium salt of 5,6-O-benzylidene-L-ascorbic acid as a white colored powder (yield 20 g). This sodium salt of 5,6-O-benzylidene-L-ascorbic acid showed the following physicochemical properties:

(i) Readily soluble in water, (ii) Specific rotation: $[\alpha]_D^{20} +24°$ (c, 1.5, H$_2$O), (iii) Decomposition point: begins to soften near 95° C. and decomposes at 130°-135° C. with bubbling. (iv) Elementary analysis:

Found: C 53.97, H 4.01 (%)

Calcd. for C$_{13}$H$_{11}$O$_6$Na: C 54.55, H 3.87 (%).

EXAMPLE 3

5,6-O-Benzylidene-L-ascorbic acid (13.2 g) was suspended in water (300 ml), to which was then added potassium hydrogen carbonate (5 g). The resulting aqueous solution was lyophilized to give a potassium salt of 5,6-O-benzylidene-L-ascorbic acid (yield 12 g) as a white colored powder which was readily soluble in water and showed decomposition point of 130°-140° C.

EXAMPLE 4

5,6-O-Benzylidene-L-ascorbic acid (13.2 g) was suspended in water (300 ml), to which was then added calcium carbonate (5 g), whereby the ascorbic acid was dissolved in water. The resulting aqueous solution was freeze-dried to give a calcium salt of 5,6-O-benzylidene-L-ascorbic acid (yield 13 g). This product was a white powdery substance which was readily soluble in water and decomposed near 200° C.

DETAILED DESCRIPTION OF THE INVENTION

Acute toxicity of the sodium salt, potassium salt or calcium salt of 5,6-O-benzylidene-L-ascorbic acid to mammals has now been affirmed to be very low through animal tests where a high dosage of the sodium salt or calcium salt was given at once either orally or intravenously to the mice. Thus, it has now been found in the animal tests that when 1000 mg/kg of the sodium salt or calcium salt of 5,6-O-benzylidene-L-ascorbic acid was given at once intravenously to ICR strain mice (5 male mice in each group, 6 week-aged and weighing 19-20 g), none of the mice thus treated died during the subsequent 2 weeks, and that when 2000 mg/kg of the sodium salt or calcium salt of 5,6-O-benzylidene-L-ascorbic acid was given at once intravenously to similar ICR strain mice (5 male mice in each group), two, on average, of the five mice thus treated died during the subsequent 2 weeks. It has further been found that when 15,000 mg/kg of the sodium salt of 5,6-O-benzylidene-L-ascorbic acid was given at once per os to similar ICR strain mice (5 male mice in each group), none of the mice thus treated died during the subsequent 2 weeks; and that when 25,000 mg/kg of the sodium salt of 5,6-O-benzylidene-L-ascorbic acid was given at once per os to similar ICR strain mice (5 male mice in each group), three, on average, of the five mice died during the subsequent 2 weeks.

After it has been affirmed through the above animal tests that the sodium salt of 5,6-O-benzylidene-L-ascorbic acid is of a very low acute toxicity upon oral and intravenous administrations to the mammals, the clinical tests have been conducted where the sodium salt of 5,6-O-benzylidene-L-ascorbic acid was administered to patients who have been suffering from some kinds of cancer-bearing diseases. All the patients as tested had volunteered for receiving the administration of the metal salts of 5,6-O-benzylidene-L-ascorbic acid before the clinical tests would have been made. As the outcomes of the clinical tests, it has now been found that the sodium salt of 5,6-benzylidene-L-ascorbic acid is effective in the clinical treatment of inhibiting the growth of cancer cells in the pancreas, liver, kidney, lymph glands, salivary glands, breast, lung and stomach.

According to this invention, therefore, there is provided a method of treating or inhibiting cancer cells grown in the pancreas, liver, kidney, lymph glands, salivary glands, breast, lung and stomach of humans, which comprises administering an effective amount of a sodium salt, potassium salt or calcium salt of 5,6-O-benzylidene-L-ascorbic acid to a human who is sufferring from the growth of cancer cells in the body of the patient.

The alkali metal or alkaline earth metal salt of 5,6-O-benzylidene-L-ascorbic acid may be given at a dosage of 10 to 200 mg/kg per day or at a dosage of 0.5 to 10 g/body (adult) per day upon parenteral administration and may be given at a dosage of 5 to 20 g/body (adult) per day upon oral administration. This active compound may conveniently be formulated into an aqueous solution in a physiological saline for intravenous injection. Appropriate dosages of the active salt of 5,6-O-benzylidene-L-ascorbic acid may vary dependently upon the curative effects to be attained on the different cancers as treated and also upon the period of time of the treatment of the cancerous diseases.

For the oral administration, the active salt of 5,6-O-benzylidene-L-ascorbic acid may be formulated into capsules, tablets, granules or powders. For the parenteral administration, said active salt may be formulated into injectionable solutions, or intravenous drip.

The content of said active salt in the formulation may vary depending on the type of the formulation as prepared. It may usually be about 0.1 to 20% by weight for oral administration and about 0.01 to 10% by weight for parenteral administration. The active salt used according to this invention may be formulated in a conventional manner into subcutaneous or intravenous injections, and also may be formulated in association with a pharmaceutically acceptable carrier, optionally together with a surface active agent, an excipient, a lubricant and other suitable additives.

This invention is now illustrated with reference to the following tests which are extracted from the protocols of the clinical treatments of patients of the cancer or tumor-bearing diseases and which have shown typical outcomes of the clinical treatment with the sodium salt of 5,6-O-benzylidene-L-ascorbic acid.

TESTS

The sodium salt of 5,6-O-benzylidene-L-ascorbic acid was dissolved in a sterilized physiological saline under sterile conditions, and the resulting aqueous solution of 1.5% by weight of said sodium salt of 5,6-O-benzylidene-L-ascorbic acid was given by intravenous drip injection to the five volunteer patients, male or female, at the dosages and for the period of treatment as indicated in Table 1 below. The protocols of the volunteers are also recorded in Table 1 below. The outcomes of the treatment of the cancer or tumor effected in the clinical tests were judged with the undermentioned gradings according to the "Japanese Criteria for Evaluation of Clinical Effects of Cancer Chemotherapy on Solid Tumors" which are as follows:

1. Complete response (CR).
    The disappearance of all known disease, determined by 2 observations not less than 4 weeks apart.
2. Partial response (PR).
    (1) 50% or more decrease in total tumor size of the bidimensionally measurable lesions which have been measured to determine the effect of therapy by 2 observations not less than 4 weeks apart.
    (2) 30% or more decrease in total tumor size of the single dimension which have been measured to determine the effect of therapy by 2 observations not less than 4 weeks apart. In addition, there can be no appearance of new lesions or progression of any lesion.
3. Minor response (MR).
    (1) 50% decrease (or 30% or more in single dimension) in total tumor size has been measured less than 4 weeks apart. (2) More than 25% and less than 50% decrease has been established bidemensionally not less than 4 weeks apart.
4. No change (NC).
   A 50% decrease (or a 30% decrease in single dimension) in total tumor size cannot be established nor has a 25% increase in the size of one or more measurable lesions been demonstrated.
5. Progressive disease (PD).
   A 25% or more increase in the size of one or more measurable lesions, or the appearance of new lesions.

The outcomes of the clinical treatment of some volunteer with the sodium salt of 5,6-O-benzylidene-L-ascorbic acid was also followed by diagnosing the treated patient according to an enzyme immunoassay method of detecting the content in serum of a carcinoembryonic antigen as commercially available under the name "CEA-EIA" (a product of Abbott Co., Limited, U.S.A.) and/or the content in serum of a sugar-chain antigen CA 19-9 which is known as a tumor marker and also known as a gastrointestinal cancer antigen specifically reactive with the mouse monochronal antibody #19-9 as commercially available for a radio-immunoassay kid preparations sold from Centocor Co. Ltd., U.S.A.

The outcomes of the clinical treatments as conducted are summarized in Table 1 below.

TABLE 1

| | | |
|---|---|---|
| Abbreviated name of volunteer treated | H. M. | T. K. |
| Sex and Age of volunteer | Female, 68-aged | Male, 68-aged |
| Nature and sites of cancer or tumor treated | Pancreatic carcinoma at pancreas | Hepatocarcinoma as transferred to liver |
| Original lesions of cancer or tumor | At the head of pancreas | Non-clarified |
| Drug administered or surgical operation made before the present test | Operation of making by-path in the cholechus duct | Adriamycin and 5-FU |
| Performance Status of volunteer before the test | 3 | 3 |
| Dosage and route of administration of the tested 5,6-O-benzylidene-L-ascorbic acid Na salt | 1.5 g to 6 g per day, intravenous | 3 g per day, intravenous |
| Administration period of the tested drug | 3 months | One month |
| Sizes or conditions of the tumor or cancer as examined under CT-scanography | 7 cm × 7 cm before test (on 24 February); 0 cm × 0 cm after test (on 22 May) | 13 cm × 8 cm before test (on 12 April); 10 cm × 6 cm after test (on 22 May) |
| Evaluation of Clinical Effects as judged | Complete response (CR) | Minor response (MR) |
| Immunoassay with CA19-9 or with CEA-EIA | 78 units of CA19-9 antigen before test decreased to 30 units after test | 3.9 units of CEA-EIA before test decreased to 2.0 units, while 190 units of CA19-9 antigen before test decreased to 60 units after test |
| Abbreviated name of volunteer treated | R. K. | D. I. |
| Sex and Age of volunteer | Male, 34-aged | Male, 55-aged |
| Nature and sites of cancer or tumor treated | Adult Wilm's tumor | Squamous cell carcinoma at submaxillary lymph glands, salivary glands and neck |
| Original lesions of cancer or tumor | At kidney | At pharnyx |
| Drug administered or surgical operation made before the present test | Cisplatin and others | Received pre-treatments |
| Performance Status of volunteer before the test | 4 | 2 |
| Dosage and route of administration of the tested 5,6-O-benzylidene-L-ascorbic acid Na salt | 3.4 g per day, intravenous | 3.0 g per day, intravenous |
| Administration period of the tested drug | 6 Days | One month |
| Sizes or conditions of the tumor or cancer as examined under CT-scanography | 25 cm × 15 cm before test (on 11 February); 15 cm × 8 cm after test (on 16 February) | Three lesions of 4.0 cm × 3.0 cm, 2.5 cm × 1.5 cm and 1.5 cm × 1.5 cm, resp., before test (on 10 |

TABLE 1-continued

| | | April); All lesions of 0 cm × 0 cm (on 13 May) after test |
|---|---|---|
| Evaluation of Clinical Effects as judged | Minor response (MR) | Partial response (PR) |
| Immunoassay with CA19-9 or with CEA-EIA | Not tested | Not changed in the normal range before and after test |
| Abbreviated name of volunteer treated | M. N. | |
| Sex and Age of volunteer | Female, 65-aged | |
| Nature and sites of cancer or tumor treated | Small cell lung carcinoma as transferred from breast | |
| Original leasions of cancer or tumor | At breast | |
| Drug administered or surgical operation made before the present test | Not received | |
| Performance Status of volunteer before the test | 4 | |
| Dosage and route of administration of the tested 5,6-O-benzylidene-L-ascorbic acid Na salt | 3.4 g per day, intravenous | |
| Administration period of the tested drug | 25 Days | |
| Sizes or conditions of the tumor or cancer as examined under CT-scanography | Lesions scattered allover before test (on 23 January); significantly reduced in number and size after test (on 17 February) | |
| Evaluation of Clinical Effects as judged | Partial response (PR) | |
| Immunoassay with CA19-9 or with CEA-EIA | Not tested | |

None of the volunteers treated as above did show any symptoms of the adverse side-effects due to the sodium salt of 5,6-O-benzylidene-L-ascorbic acid administered. From the results of the clinical tests as shown in Table 1 above, it has been surprisingly been revealed that the sodium salt of 5,6-O-benzylidene-L-ascorbic acid is effective to treat or inhibit the cancer or tumor cells of different sorts in humans "Performance Status" shown in the above table is to estimate the general physical conditions of the volunteer patients to be treated and the "Performance Status" are evaluated in the following grades:

| Grades | Performance Status |
|---|---|
| 0 | Patient as treated does not show any symptoms of the disease in appearance, and is able to make social activities and behave as similarly as do before the outbreak of the disease, without restrictions. |
| 1 | Patient does show a low degree of the symptoms of the disease and is able to make walking, weak labors or sedentary work such as light household affairs and writing work, but is prohibited from doing physical labor. |
| 2 | Patient is able to do walking and looking-after-oneself, with ocassional needing personal assistance, and he or she lives outside the bed for a time of 50% or more of the period of one day. |
| 3 | Patient is able to look after oneself to a limited degree but with frequently needing personal assistance, and he or she has to stay in bed for a time of 50% or more |

| Grades | Performance Status |
|---|---|
| | of the period of one day. |
| 4 | Patient is not able to look after oneself and always needs personal assistance and has to stay in bed over the day. |

What is claimed:

1. A method of inhibiting a carcinoma or tumor grown in the pancreas, lymph glands, salivary glands or lung, which comprises orally or parenterally administering a carcinoma-inhibiting effective amount of a sodium salt of 5,6-O-benzylidene-L-ascorbic acid to the carcinoma-bearing patient.

2. A method of inhibiting a carcinoma or tumor grown in the liver or kidney, which comprises orally or parenterally administering a carcinoma-inhibiting effective amount of a sodium salt of 5,6-O-benzylidene-L-ascorbic acid to the carcinoma-bearing patient.

3. A method of inhibiting a carcinoma or tumor grown in the stomach, which comprises orally or parenterally administering a carcinoma-inhibiting effective amount of a sodium salt of 5,6-O-benzylidene-L-ascorbic acid to the carcinoma-bearing patient.

4. A method of decreasing of the total size of pancreatic carcinoma by 50% or more in the bidimensions of the tumor lesion when twice observed at a time interval of not less than four weeks apart, which comprises administering orally or parenterally an effective amount of a sodium salt of 5,6-O-benzylidene-L-ascorbic acid of the formula

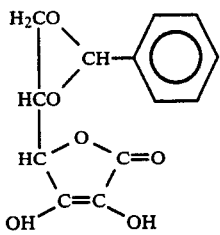

to a pancreatic carcinoma-bearing human patient.

5. A method of decreasing the total size of squamous cell carcinoma between 25–50% in the single dimension of the tumor lesion when twice observed at a time interval of not less than four weeks apart, which comprises administering orally or parenterally an effective amount of a sodium salt of 5,6-O-benzylidene-L-ascorbic acid to a squamous cell carcinoma-bearing human patient.

6. A method of decreasing the total size of small cell lung carcinoma between 25–50% in the single dimension of the tumor lesion when twice observed at a time interval of not less than four weeks apart, which comprises administering orally or parenterally an effective amount of a sodium salt of 5,6-O-benzylidene-L-ascorbic acid to a small cell lung carcinoma-bearing human patient.

7. A method of decreasing the total size of hepatocarcinoma between 25–50% in the single dimension of the tumor lesion when twice observed at a time interval of not less than four weeks apart, which comprises administering orally or parenterally an effective amount of a sodium salt of 5,6-O-benzylidene-L-ascorbic acid to a hepatocarcinoma-bearing human patient.

8. A method of decreasing the total size of Adult Wilm's tumor between 25–50% in the single dimension of the tumor lesion when twice observed at a time interval of not less than four weeks apart, which comprises administering orally or parenterally an effective amount of a sodium salt of 5,6-O-benzylidene-L-ascorbic acid to an Adult Wilm's tumor-bearing human patient.

* * * * *